United States Patent [19]
Starling, Jr. et al.

[11] Patent Number: 6,090,867
[45] Date of Patent: Jul. 18, 2000

[54] ORTHODONTIC ADHESIVE

[75] Inventors: Kenneth Edward Starling, Jr., Decatur; Brian James Love, Jefferson, both of Ga.

[73] Assignee: Georgia Tech Research Corporation, Atlanta, Ga.

[21] Appl. No.: 08/019,616

[22] Filed: Feb. 19, 1993

[51] Int. Cl.[7] .................................................... A61F 2/00
[52] U.S. Cl. ........................ 523/113; 523/118; 524/296
[58] Field of Search ................................ 523/113, 118; 524/296, 297; 433/9

[56] References Cited

U.S. PATENT DOCUMENTS

| | | | |
|---|---|---|---|
| 4,010,545 | 3/1977 | Kilian et al. | 433/9 |
| 4,222,923 | 9/1980 | Rhodes et al. | 524/296 |
| 4,340,529 | 7/1982 | Lee, Jr. | 433/9 |
| 4,479,782 | 10/1984 | Orlowski et al. | 433/9 |
| 4,525,234 | 6/1985 | Herold et al. | 524/296 |
| 5,154,613 | 10/1992 | Cohen | 433/9 |

FOREIGN PATENT DOCUMENTS

| | | | |
|---|---|---|---|
| 1085269 | 3/1989 | Japan | 524/296 |

OTHER PUBLICATIONS

Love, Hochman & Starling, Jr., "Orthodonitic Adhesive Modification to Enhance After–Treatment Removal"–Feb. 20, 1992–(2).

Love, Starling, Jr. & Baughn "On Controlling Adhesion of Orthodontic Adhesives through Adjustment of the Interphase Mechanical Properties"–(1993)–(4).

Odegaard & Segner "Shear Bond Strength of Metal Brackets Compared with a New Cermanic Bracket"–(1988)–(4).

Ostertag, Dhuru, Ferguson & Meyer, Jr.–"Shear, Torsional, and Tensile Bond Strengths of Ceramic Brackets Using Three Adhesive Filler Concentrations"–(1991) –(5).

Strobl, Bahms, Williams, Bishara & Stwalley "Laser–Aided Debonding of Orthodontic Ceramic Brackets"–(1992) –(4).

Gwinnet –A Comparison of Shear Bond Strengths of Metal and Ceramic Brackets –(1988) –(2).

Ruggeberg & Lockwood –"Thermal Debracketing of Orthodontic Resins" (1900) –(5).

Storm –"Debonding Ceramic Brackets"–(2,1990) –(3).

Sheridn, Brawley & Hastings –"Electrothermal Debracketing"–(1986) –(4).

Sheridan, Brawley & Hastings –"Electrothermal Debracketing, Part II, An In–Vivo Study"–(1986) –(3).

Williams & Edmundson –"Orthondontic Tooth Movement Analyzed by the Fimite Element Method"–(1984) –(5).

Fotos, Spyrakos & Bernard –"Orthodontic Forces Generated by a Simulated ARchwire Appliance Evaluated by the Fimite Element Mehtod"–(date unknown) –(4).

Swartz –"A Technical Bulletin on the Issues of Bonding and Debonding Ceramic Brackets"(4,1–15,1988) –(7).

*Primary Examiner*—Paul R. Michl
*Attorney, Agent, or Firm*—Oldham & Oldham, LPA

[57] ABSTRACT

An adhesive system has been developed for orthodontic ceramic brackets which minimizes tooth fracture and makes bracket removal easier and more predictable. The adhesive system makes use of current filled adhesives and a plasticizer (e.g. diethyl phthalate, xylene, etc.). Additions of plasticizer between 10 to 20 weight percent of the adhesive will decrease the adhesion in excess of 50%. This adhesive permits more patient comfort while at the same time allowing for the use of ceramic brackets.

3 Claims, 4 Drawing Sheets

ORTHODONTIC ADHESIVE

TECHNICAL FIELD

The invention described herein pertains generally to an orthodontic adhesive modification to enhance after-treatment removal of ceramic brackets from a user's teeth.

BACKGROUND OF THE INVENTION

The introduction of ceramic orthodontic brackets, made from single crystal or polycrystalline sapphire is seen as a major advancement in the aesthetics of orthodontic treatment, compared to the existing stainless steel brackets. Unfortunately, there are problems with the ceramic systems. The most serious of the drawbacks occurs during the bracket removal after orthodontic treatment is complete.

Several problems occur during the removal process. Higher forces are required to remove ceramic brackets than the metal brackets from the teeth. This is attributed to the peeling mechanism used to remove the metal bracket that is not available for the ceramic bracket. In the ceramic system, all three components (the bracket, the enamel, and the highly ceramic filled polymer resin) are strong and brittle. These higher forces have at times, exceeded the strength of either the bracket itself, or more importantly the enamel to which the bracket is bonded. If the bracket fractures, diamond drilling of the residual ceramic is required for removal. If the enamel fractures, an expensive restorative dental procedure is required to repair the fractured region. Either procedure is time consuming and stressful for both the patient and the dentist. "Enamel crazing" has been reported as an additional sign of the brittle removal of these brackets. While crazing does not lead to an immediate need for restorative care, it does indicate enamel damage. There is a real need to make the removal process easier and more predictable.

There have been a number of efforts aimed at facilitating the removal process. Bracket manufacturers have attempted to place deliberate flaws within the brackets base to cause a lower strength failure within this region during removal. However, placing stable flaws within the ceramic is not trivial or inexpensive. Other efforts have looked at different removal techniques (i.e. torsional and shear modes). Another technique under development involves the use of a heated tool to lower the modulus and tensile strength of the adhesive during removal, but considering the potential tooth pulp damage while heating the adhesive, widespread use of these instruments has not developed.

In order to solve the problems with the prior art solutions to the problem, a modification of the polymeric adhesive mechanical properties has been achieved through a controlled interaction with plasticizers, thereby selectively permitting control over the removal forces by predicating the failure mode of the adhesive as being a ductile failure mode rather than a brittle failure mode. cl SUMMARY OF THE INVENTION In accordance with the present invention, there is provided an orthodontic adhesive wherein the modulus of the filled ceramic adhesive can be tailored through the use of selected plasticizers with likely FDA approval.

It is an object of this invention to provide an adhesive wherein increases in the plasticizer content of the adhesive lead to lower measured adhesion values when bonded to a standard substrate.

It is still another object of this invention to make removal of the more aesthetically pleasing ceramic brackets easier and more predictable through a ductile failure mechanism within the adhesive, rather than the current brittle mechanism.

These and other objects of this invention will be evident when viewed in light of the drawings, detailed description, and appended claims.

DETAILED DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

Figure 1:
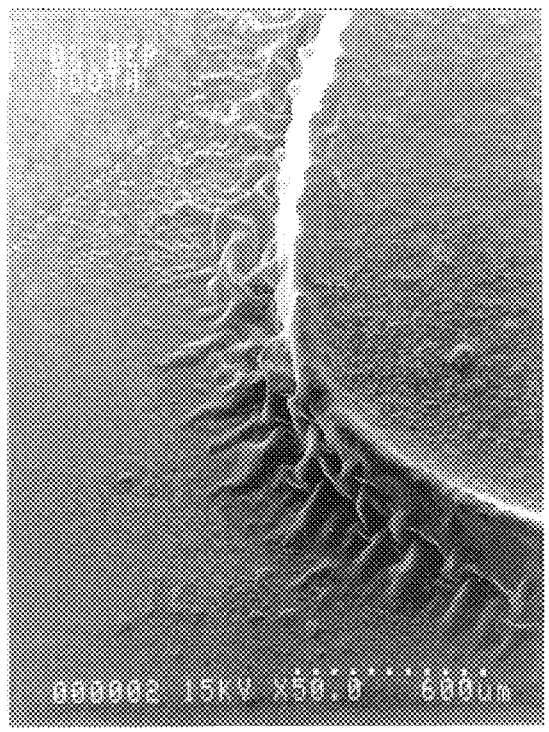
FIG. 1 is an electron micrograph showing the corner region of a bracket/tooth assembly where the bracket is removed using an unplasticized Reliance Orthodontics Phase II® adhesive.

Referring now to the drawings wherein the showings are for purposes of illustrating the preferred embodiment of the invention only and not for purposes of limiting the same, the Figures show the ability to modify the fracture zone from one with a brittle failure mechanism to a ductile failure mode, thereby permitting easier removal of ceramic brackets from an enameled tooth with less restorative procedures necessary to the tooth surface.

Figure 6:
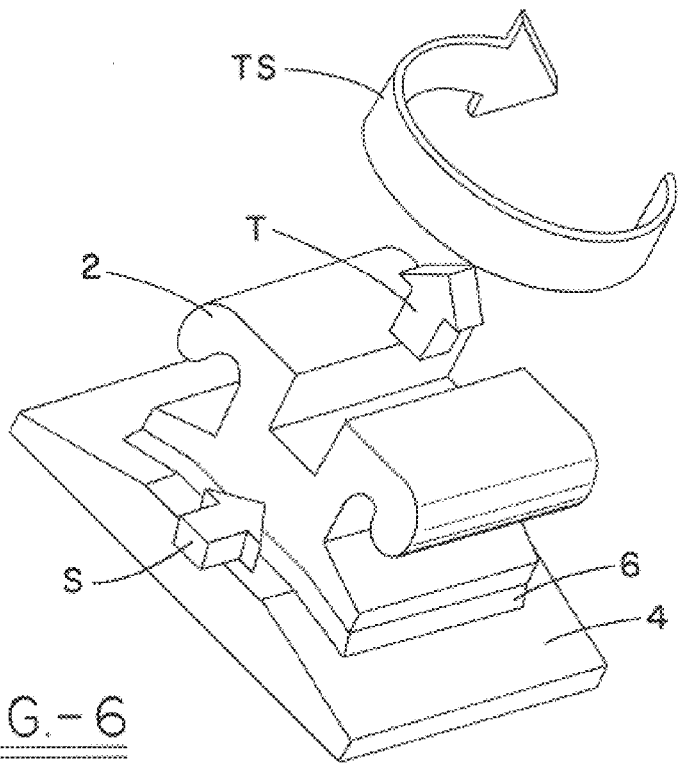
FIG. 6 is a perspective view of a ceramic bracket as it would be attached to a substrate (tooth or wire mesh) and the types of force applicable to remove the ceramic bracket.

New materials used in orthodontics have created some new challenges in dental adhesives. The major change in orthodontic materials has been the switch from stainless steel anchoring schemes to ceramic ones. As shown in FIG. 6, there are several different forces at play when a ceramic bracket 2 is debonded and removed from a substrate 4 which had previously been bondingly attached via a resin adhesive 6. A shearing force S is directed in a plane parallel to the plane of the substrate. A tensile force T is directed in a plane normal to the surface of the substrate, and a torsional shear force TS is directed as a torque about a fulcrum point in a plane parallel to that of the substrate.

While ceramic brackets are more aesthetically pleasing since they are typically more closely matched in color to that of a natural tooth, higher forces are required to remove them after the treatment period is complete. This has led to bracket fractures (more time consuming for the orthodontist) and to tooth enamel fractures which can result in costly additional treatment. Thus, there has been a real interest in designing an adhesive and bracket system which would allow for more predictable and easier removal.

Most of the commercial adhesive systems for these applications are based on acrylic cements with a large ceramic filler content (ranging up to 90% of the adhesive weight). There are only three ways which can be used to soften the adhesive. One is to simply remove some or all of the filler particles. But removing the filler particles, makes the cement less paste-like in its consistency, a desirable characteristic to most orthodontists. Another is to heat the adhesive with a heated removal tool, but this is unsafe at the temperatures required to soften the adhesive (often above 100° C.). The last approach includes the use of a safe plasticizer to swell the adhesive and make it ultimately less stiff.

Since the adhesive is in immediate contact with the saliva in the mouth, commercial adhesive systems which have already passed the necessary FDA testing for an oral material were used. Furthermore, any chosen plasticizer has to additionally be readily classified in a similar FDA category. One such plasticizer is diethyl phthalate, a common plasticizer in blood bags, for which some toxicological data exists to support its non-hazardous claims.

Figure 5:
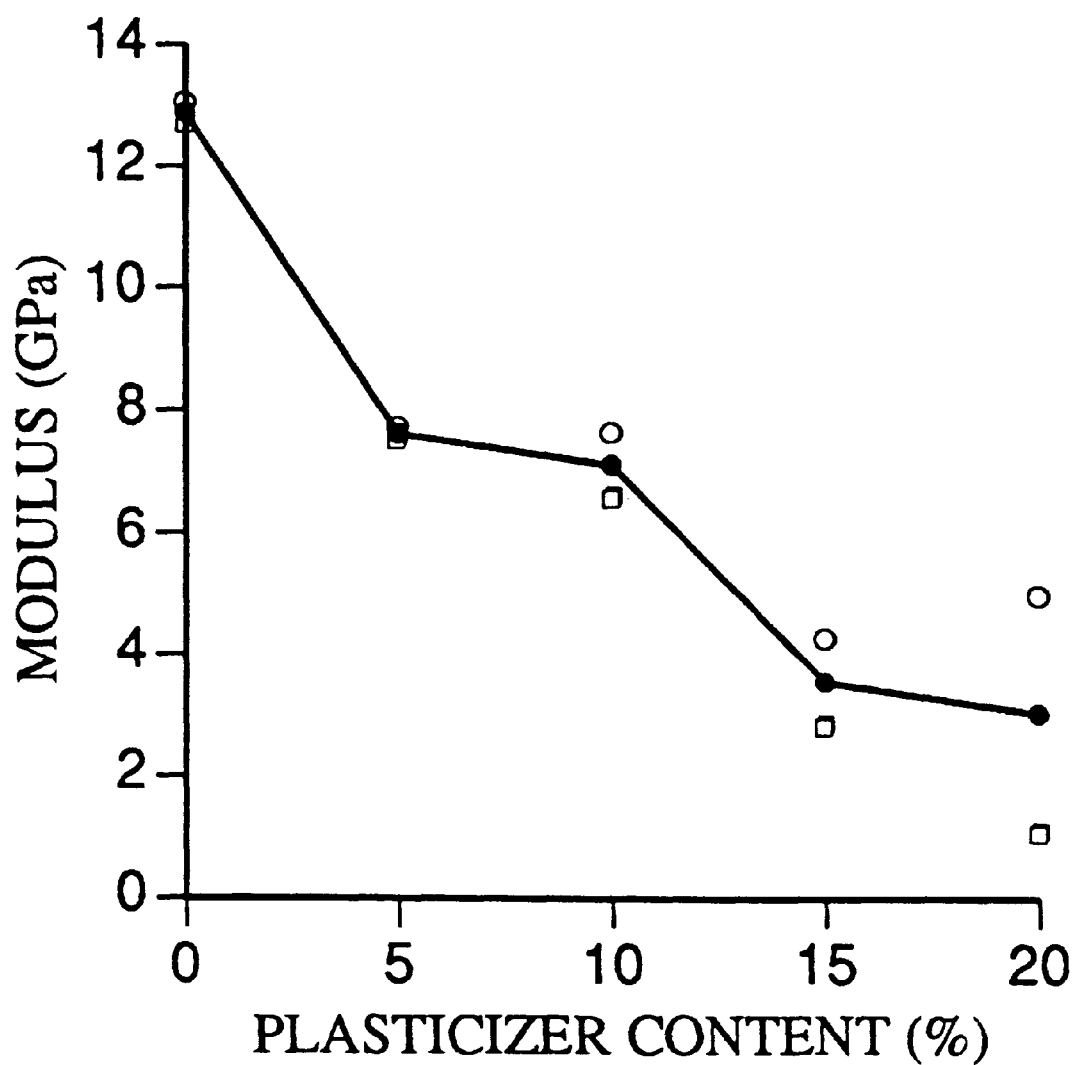
FIG. 5 is a graph of modulus (GPa) vs. plasticizer content (weight %)

As seen in FIG. 5, which is a graph of the results obtained by adding a diethyl phthalate plasticizer to a commercially available adhesive, such as produced by Reliance Orthodontics of Itasca, Ill., sold under the tradename Phase II® two component cement containing paste A, (a bis-GMA, polyethyleneglycol dimethacrylate, amine/hydrofluoride copolymer resin with quartz and silica glass filler), and paste B, (a bis-GMA, polyethyleneglycol dimethacrylate, benzoyl peroxide initiator with quartz and silica glass filler) and using it as recommended with diethylphthalate, between 0 and 20% of the adhesive weight being mixed with a 50/50 mixture of the two components of the Phase II® cement. The curve indicates that the modulus is a function of the plasticizer content in the adhesive formulation. Dramatic changes in the modulus, the resistance to deformation, with increasing plasticizer content, are evident. Additionally, as seen in Table I wherein limited tensile strength data is shown, a reduction in the stiffness of the adhesive through the incorporation of a plasticizer is clearly indicated.

TABLE I

Tensile Strength as a Function of Plasticizer Weight Percent

| % plasticizer[1] | 0% | 10% |
|---|---|---|
| tensile strength (psi) | 6305 | 2769 |

[1]diethyl phthalate

The tensile bars were a mold of a glass microscope slide made in polyvinyl siloxane impression material. This impression was lined with aluminum foil and subsequently loaded with the desired amount of adhesive. A clean glass slide was used to cover the sample to provide an equal thickness and reduce air bubbles. A weight was used to hold the slide in place during the curing.

Figure 4:
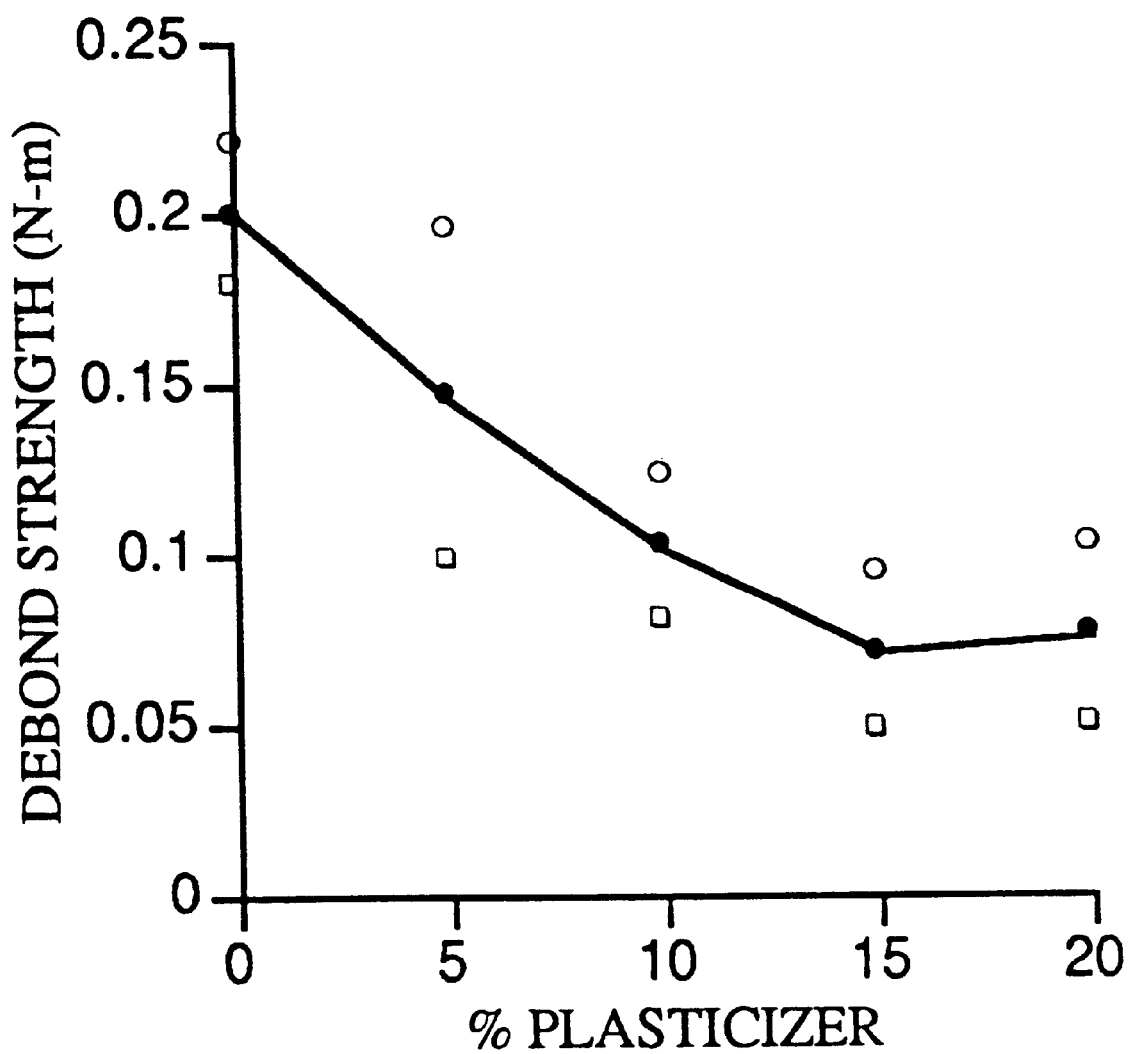
FIG. 4 is a graph of torque force (N-m) for removal vs. plasticizer content (weight %)

This mechanical property data becomes more meaningful, when viewed in context with FIG. 4 which is a graph of bracket adhesion vs. the plasticizer content. The torque forces required to remove these brackets significantly decreases with increasing plasticizer in the adhesive. Thus, a tailorable adhesive formulation for use in orthodontic applications has been developed for use with the new types of ceramic brackets.

Figure 3:
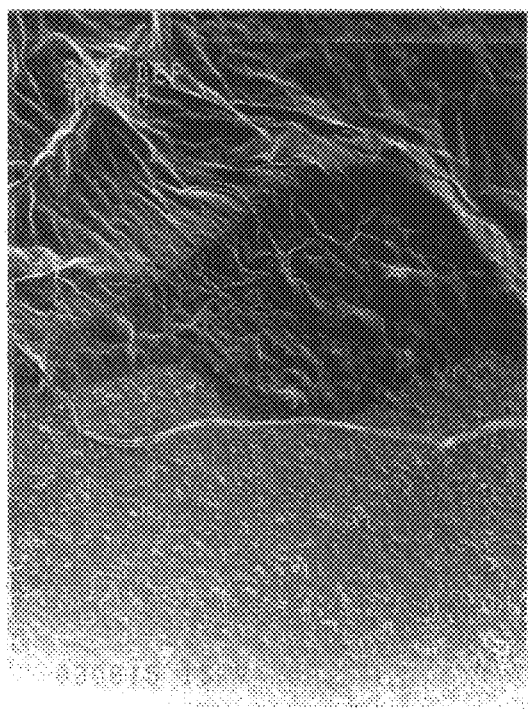
FIG. 3 is an electron micrograph showing a similar region to that shown in FIG. 1, wherein the adhesive is treated with 20 weight % diethyl phthalate as a plasticizer.

Of significance is the mechanism of the lower removal forces, aiding in the determination of why less force is required to remove brackets using this modified adhesive than with the normal adhesive. Electron micrographs seen in FIGS. 1 and 3 offer some insight into this matter. The bracket which was bonded to the region in FIG. 1 was bonded using a normal adhesive, while the bracket region shown in FIG. 3 was bonded using the plasticized adhesive. The left side and bottom of the picture represent the tooth region and the right upper corner represents the corner of the glue on which the bracket sat. The highest stress areas in a torque stress are in the corners. As shown in FIG. 1 where no added plasticizer was incorporated into the adhesive, there is a clean fracture at the glue/bracket interface with no dissipative forces within the adhesive resin. By comparing the micrograph of Fig. 1, with that in FIG. 3, there is a different fracture zone in the plasticized interface. In fact, the fracture zone tends to force its way into the adhesive and away from the bracket which is the fracture zone within the normal adhesively bonded bracket. In viewing FIG. 3, there is a large depression in the corner regions of the adhesive representing fracturing through the adhesive, in these cases, the weakest point of the assembly.

Figure 2:
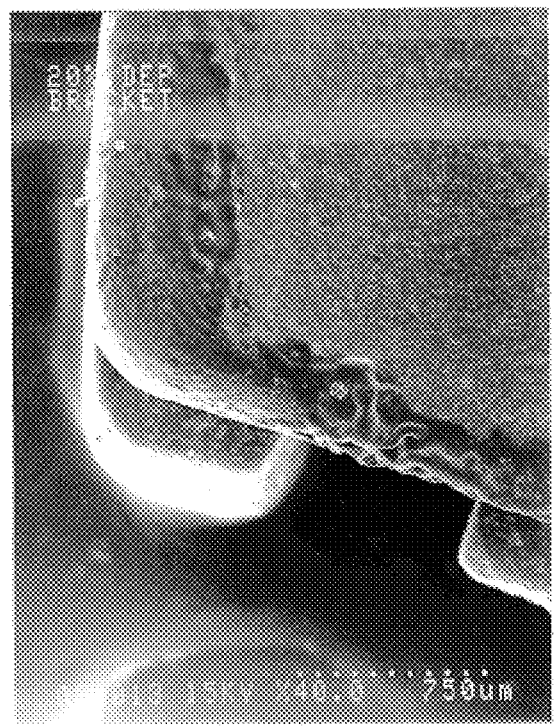
FIG. 2 is an electron micrograph showing the corner region of a bracket where the adhesive used in FIG. 1 is treated with 20 weight % diethyl phthalate.

As corroborative evidence, FIG. 2 shows residual adhesive on the bonded side of the bracket. Thus, the plasticizer changes the fracture point from the bond line between adhesive resin and the bracket to one within the resin in the high stress regions (i.e., the corners). Thus, not only is there strong evidence that this modified adhesive is less stiff, but also indicates that the failure mode is also different. These electron micrographs indicate that the failure mode of the adhesive can be shifted as being a ductile failure mode rather than a brittle failure mode.

EXAMPLE 1

The adhesive investigated was a two component methacrylate-based adhesive with a benzoyl peroxide curing agent from Reliance Orthodontic Products, Inc., sold under the tradename of Reliance Phase II®. The paste adhesive was filled up to 75 weight percent with 0.5 µm silica particles. Plasticizer additions of diethyl phthalate were made and measurements of the mechanical property variations and adhesive response were taken as a function of the plasticizer content.

The modulus measurements were made using a Polymer Laboratories Dynamic Mechanical Thermal Analyzer (DMTA) using a frequency of 10 Hz. The dynamic modulus characterization was performed from temperatures ranging from 30° C. to 200° C. at a frequency of 10 Hz. At least three samples at each plasticizer concentration were tested.

For the adhesion tests, ceramic brackets from two manufacturers were obtained, GAC International Allures® brackets of Central Islip, N.Y., and Rocky Mountain Orthodontic, RMO® Signature brackets of Denver, Colo. To overcome concern about enamel variations, a stainless steel wire mesh disk was used as a standard substrate. As a confirmation, several upper incisors from extractions were also used in the adhesive tests.

The teeth were etched with a 40% $H_3PO_4$ gel for 15 seconds, followed by a water rinse and air drying. The teeth and the disks were first painted in the bonding area using an unfilled polymethyl methacrylate (PMMA) sealer. The adhesive, (with appropriate amount of plasticizer added) was then manually mixed and applied to the base of the bracket. The bracket was ten bonded to the substrate and any excess was removed. The set times varied from 2 to 5 minutes. The bonded brackets were allowed to set for 24 hours before testing. The removal force measurements were taken in a torsional shear mode with a torque meter attached to measure the peak torque during removal. The torque meter was a Sturtevant 5 in-lb meter.

TABLE II

| Debond Strength from Standard Metal Substrate (in-1b) | | | | | |
|---|---|---|---|---|---|
| % plasticizer[(1)] | 0% | 5% | 10% | 15% | 20% |
| Avg. Debond strength | 1.76 | 1.29 | 0.89 | 0.62 | 0.66 |
| Standard Deviation | 0.19 | 0.43 | 0.19 | 0.21 | 0.23 |
| Nbr. of Samples | 10 | 9 | 10 | 9 | 10 |

[(1)]diethyl phthalate

The plasticizer's effect on this adhesive is analogous to its effect on bulk polymers. There is a significant softening of the plasticized adhesive modulus, due to the polymer-plasticizer interaction. This effect occurs even though the adhesive is heavily filled with silica. The plasticizer within the adhesive significantly lowers the observed peak torque required for bracket removal from the standard substrate. The observations indicate that the increased plasticizer concentration makes cohesive ductile fracture within portions of the adhesive more likely. Given that the overall goal of this effort is to make bracket removal easier and more predictable, moving the fracture zone within the adhesive has contributed to a safer removal of the ceramic bracket While dialkyl phthalates have been discussed primarily so far, there are other plasticizers which will effectively accomplish the desired effect.

EXAMPLE 2

Xylene was added to a Reliance Phase II® two component cement under plasticization conditions of 5 weight percent and 10 weight percent. The modulus at two different frequencies under the two plasticization conditions is shown in Table III.

TABLE III

| Modulus at Different Frequencies using Xylene Plasticizer | | | |
|---|---|---|---|
| plasticizer xylene[(1)] | 0% | 5% | 10% |
| modulus @ 10 Hz | 12 GPa | 5.62 GPa | 4.26 GPa |
| modulus @ 1 Hz | | 5.01 GPa | 3.98 GPa |

[(1)]amount of plasticizer xylene added to orthodontic adhesive Phase II ® supplied by Reliance Orthodontics, Itasca Illinois.

The modulus was measured by a Dynamic Mechanical Thermal Analyzer at room temperature at frequencies of 10 Hz and 1 Hz. The effect of added plasticizer at levels of both 5 and 10 weight percent in comparison to an unplasticized adhesive (12 GPa) is similar in effect to that observed for the diethyl phthalate plasticizer.

DISCUSSION

There are two important considerations in identifying a suitable plasticizer for dental material applications. One relates to plasticizer efficacy and the other is the use environment.

Generally, a plasticizer is a low molecular weight solvent capable of existing in the polymer structure without reacting with it. Plasticizers usually have an attractive interaction with the polymer which allows the polymer chains to act more independently of one another. Characteristics of plasticized polymers include lower transition temperatures, reduced modulus and increased molecular motion. There is also usually an observed increase in free volume within the polymer related to the increase in the number of plasticizer/polymer interaction points.

Thermodynamics however, only discusses whether a solvent will act as a plasticizer. The use environment additionally plays a role in selecting the right plasticizer for a particular application. There are three considerations for dental polymer plasticization. The first is the use temperature of the oral environment, which is roughly 37° C., and care must be given to select a plasticizer which will not volatilize at this temperature. The second is that the plasticized polymer must have little solubility with water and saliva to prevent extraction and preserve the plasticizing effect. And lastly, since dental polymers are intimately in contact with the body, care must be given to make sure that the plasticizer selected is not acutely toxic in the doses to be used in conjunction with the polymer.

One selection tool in identifying which solvent would be a good candidate plasticizer is its solubility parameter. To a first approximation, this parameter is related to the energy required to separate two solvent molecules from each other. There are polar contributions, non-polar contributions, and other factors such as hydrogen bonding which contribute to this energy. Solvents whose solubility parameter nearly matches that of the polymer should be good candidate solvents. For example, polymethyl methacrylate, the base material for the polymer in most dental applications, has a solubility parameter of 9.5 Hildebrands, or about 19.0 MPA$^{1/2}$. A window of solubility parameters from about 17.5 MPA$^{1/2}$ to about 22.5 MPA$^{1/2}$ includes a number of possible solvents which would be thought to have a similar effect to interact with the polymer and reduce its stiffness. These solvents include organic esters (e.g. diethyl phthalate), aromatic and halogenated hydrocarbons (e.g. xylene), ketones and glycol ethers.

In a preferred embodiment, the phthalate esters are used as the plasticizer of choice, particularly for their proven track record in biomaterials applications. Toxicological work has already been performed regarding their use in plasticizing polymers for blood bag applications, where the amount of free plasticizer is thought to be significantly higher. Their boiling points are well above 200° C., which is an additional advantage since this would limit their volatility at the temperatures experienced within the oral cavity.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A dental adhesive system which permits easier removal of ceramic brackets from an enameled tooth surface comprising:

(a) an orthodontic adhesive which bonds a ceramic bracket to the enameled tooth surface; and (b) a plasticizer added to the orthodontic adhesive which promotes a ductile failure mechanism within the adhesive rather than a brittle mechanism when debonding the ceramic bracket, the plasticizer having a low vapor pressure at a temperature of an oral cavity thereby not significantly volatilizing at this temperature, the plasticizer having little solubility with water and saliva to prevent extraction and preserve the plasticizing effect, the plasticizer not being acutely toxic in the doses to be used in conjunction with the adhesive; wherein the adhesive further comprises a ceramic filler.

2. The dental adhesive system of claim 1 wherein the ceramic filler content of the adhesive if from about 0.01 weight percent to about 90 weight percent.

3. A dental adhesive system which permits easier removal of ceramic brackets from an enameled tooth surface comprising:

(a) an acrylate-based orthodontic adhesive curable without the application of any supplemental heat, which bonds a ceramic bracket to the enameled tooth surface; and (b) a plasticizer added to the orthodontic adhesive which promotes a ductile failure mechanism within the adhesive rather than a brittle mechanism when debonding the ceramic bracket, the plasticizer having a low vapor pressure at a temperature of an oral cavity thereby not significantly volatilizing at this temperature, the plasticizer having little solubility with water and saliva to prevent extraction and preserve the plasticizing effect, the plasticizer not being acutely toxic in the doses to be used in conjunction with the adhesive, the plasticizer having a solubility parameter from about 17.5 $MPA^{1/2}$ to about 22.5 $MPA^{1/2}$.

* * * * *